United States Patent [19]

Steer

[11] Patent Number: 4,568,339

[45] Date of Patent: Feb. 4, 1986

[54] FEMALE INCONTINENCE DEVICE

[75] Inventor: Peter L. Steer, Surrey, England

[73] Assignee: Craig Medical Products, Limited, East Grinstead, England

[21] Appl. No.: 546,350

[22] Filed: Oct. 28, 1983

[30] Foreign Application Priority Data

Nov. 5, 1982 [GB] United Kingdom ............... 8231719
Nov. 5, 1982 [GB] United Kingdom ............... 8231720
Nov. 5, 1982 [GB] United Kingdom ............... 8231638

[51] Int. Cl.[4] .............................................. A61F 5/44
[52] U.S. Cl. .................................... 604/329; 4/144.3
[58] Field of Search ................ 4/206.24, 206.25, 760, 4/761, 144.1-144.4; 604/327-331

[56] References Cited

U.S. PATENT DOCUMENTS

| 1,951,871 | 3/1934 | Judah | 4/144.3 |
|---|---|---|---|
| 2,483,079 | 9/1949 | Williams | 128/295 |
| 2,490,969 | 12/1949 | Kinyon | 604/329 |
| 3,194,238 | 7/1965 | Breece | 128/295 |
| 3,374,790 | 3/1968 | Mayhorne | 128/295 |
| 3,512,185 | 5/1970 | Ellis | 4/110 |
| 3,613,122 | 10/1971 | Gross et al. | 4/110 |
| 3,661,155 | 5/1972 | Lindan | 128/295 |
| 3,776,235 | 12/1973 | Ratcliff et al. | 128/295 |
| 3,995,329 | 12/1976 | Williams | 4/110 |
| 4,067,335 | 1/1978 | Silvanov | 128/283 |
| 4,116,197 | 9/1978 | Bermingham | 128/286 |
| 4,194,508 | 3/1980 | Anderson | 128/295 |
| 4,198,979 | 4/1980 | Cooney et al. | 128/295 |
| 4,202,058 | 5/1980 | Anderson | 4/144.3 |
| 4,270,539 | 6/1981 | Michaud | 128/295 |
| 4,495,951 | 1/1985 | Kenda | 4/144.3 |
| 4,496,355 | 1/1985 | Hall et al. | 604/327 |

FOREIGN PATENT DOCUMENTS

| 56318 | 7/1982 | European Pat. Off. . | |
|---|---|---|---|
| 1766795 | 1/1971 | Fed. Rep. of Germany . | |
| 7202092 | 8/1973 | Netherlands | 604/330 |
| 1144483 | 5/1969 | United Kingdom . | |
| 1193261 | 5/1970 | United Kingdom . | |
| 1422638 | 1/1976 | United Kingdom . | |
| 2072512 | 3/1981 | United Kingdom . | |
| 2070936 | 9/1981 | United Kingdom . | |

Primary Examiner—J. L. Kruter
Attorney, Agent, or Firm—Lawrence S. Levinson; Robert E. Lee, Jr.

[57] ABSTRACT

A female incontinence device having a pair of deflectable walls defining a groove at the periphery of the device intended to contact the wearer. The device as seen in plan has a waisted or 8-shaped configuration and the deflectable walls as seen in side elevation have sealing edges each of which is constituted by a pair of continuous curves, one on each side of the central longitudinal axis of the device and which extend from a high point at the front of the device to a high point at the rear of the device. An undercut region is located beneath the deflectable walls to limit any splashing of discharged urine. A gasket or adhesive material can be disposed within the groove.

13 Claims, 8 Drawing Figures

FEMALE INCONTINENCE DEVICE

BACKGROUND OF THE INVENTION

The prior art is replete with attempts to design a completely satisfactory female incontinence device. One of the greatest problems involved is obtaining adequate and reliable sealing of the device to the skin of the wearer, bearing in mind the complex shape and numerous variations from person to person of the relevant part of the female anatomy.

The following patents and patent applications are exemplary of the previous designs of female incontinence devices. Williams in U.S. Pat. No. 2,483,079 describes a device 10 comprising a substantially cylindrical hollow body 16. An upwardly tapered lower surface 17 is formed on body 16 to facilitate its positioning in the vagina. An end plate 18 is secured to the other end of body 16. A discharge tube 21 is secured and protrudes from end plate 18. A suspensory belt is provided to aid in retaining device 10 in position.

Breece in U.S. Pat. No. 3,194,238 discloses a female incontinence device comprising a support means 11 which carries a tubular fitting 12. Means 11 is connected to a series of straps. Fitting 12 is adapted to be internally inserted between labia of the vulva for sealing engagement under slight pressure with surfaces surrounding the urethral orifice. The support means 11 has side walls of selected configuration for engagement with external surfaces of the labia of the vulva. The tubular member communicates through a port in the support member with a suitable drain tube which may conduct discharge to a suitable bag or receptacle.

Mayhorne in U.S. Pat. No. 3,374,790 discloses a belt supported female incontinence device. The device includes an arcuate shaped sheet 20 having a pad of flexible polymeric foam 28 surrounding an opening 26. Opening 26 leads to a funnel-like receiver 40 which in turn leads to a tube 42.

Ellis in U.S. Pat. No. 3,512,185 discloses a female urinary collection device. The device includes a forward lip normally fitting below the clitoris, U-shaped guards capable of being impressed against the introitus, a hollow body to collect urine, portions of said body capable of being enfolded by the labia minora when in position, and a runoff spout to funnel the urine to a depository.

Gross et al. in U.S. Pat. No. 3,613,122 disclose a female urination device comprising a tapering body portion connecting into an elongated discharge tube. The body portion includes a lip whereby in use urine is directed into the body portion to be discharged through the tube with the lip positioned against the body to prevent any backward dripping of urine.

Lindan in U.S. Pat. No. 3,661,155 disclosed a female incontinence device including a pessary-like support, a deformable loop extending outwardly from the support and a flexible container removably secured to an opening through the loop. The deformable loop is adapted to encircle the urethral orifice of a wearer to hold the container in a desired position when the pessary-like support is received and retained within the vagina.

Ratcliffe et al. in U.S. Pat. No. 3,776,235 disclose a female incontinence device comprising a collection and funneling container and a retaining member fixed to said container adapted for removable insertion in the vagina. The retaining member 10 is positioned in a manner such that when inserted into the vagina, the container is disposed at the urethral orifice without being in contact therewith.

Williams in U.S. Pat. No. 3,995,329 discloses a female urinary device comprising a body having an elongated lower portion with a fluid discharge passageway and an upper portion which has continuous sealing walls. Each side wall fits between a labia minora and a spread labia majora. The front wall is disposed slightly forward of the preputium clitoridis and the rear wall is disposed slightly forward of the pars intermedia. Side walls are concavely curved to generally match but somewhat distort abutted flesh.

Bermingham in U.S. Pat. No. 4,116,197 discloses a female incontinence device which consists of an adjustable belt having a flexible sheet attached thereto. A urine collection pouch depends from the sheet with a disposable vaginal pad provided between the wearer's body and the sheet.

Anderson in U.S. Pat. No. 4,194,508 discloses a female incontinence device which includes a substantially closed housing having an opening for an ingress conduit with a flexible cup-like diaphragm to fit over the urethral opening. The housing has a further opening along the length thereof to direct urine to a collection receptacle. The housing is of relatively small size as so to be substantially self supported by entrapment by at least partial covering thereof by the labial folds when positioned for use.

Cooney et al. in U.S. Pat. No. 4,198,979 disclose a female incontinent device comprising a one piece generally funnel shaped rigid collection means. There is provided a flanged lip forming a seat around the wider orifice of the collection means shaped so that the outer surface of the flanged lip when covered with a layer of adhesive can be snugly placed against the vestibule of the user and at least a portion of the inner surface of the flanged lip will be covered by the labia minora of the user to permit its normal pressure to urge the collection means against the vestibule. Preferably, a portion of the surface of the flanged lip of the collection means is warped upwardly to form a pommel which is insertable into the vagina of the user to both prevent backward movement of the device and to assist in channeling urine.

Michaud in U.S. Pat. No. 4,270,539 discloses a female urine collection device having an interface body comprising a forward portion defining a urine receiving bore having an inlet in the interface surface adapted to surround the urethral opening and a rear portion having a non-invasive vaginal seal on the interface surface for sealing the vagina of user from communicating with the urine receiving bore. An absorbent pad is removably supported on the interface body and extends laterally therefrom. Also disclosed is a garment for supporting the device.

Vincent in British Pat. No. 1,144,483 discloses a female incontinence device comprising an oval sealing ring secured to a platform which, apart from a peripheral margin is stiff so that the sides of the sealing ring which run in directions generally parallel to the major axis of the oval are prevented from closing upon one another. An outlet orifice is provided at the rear of the platform. The surface of the sealing ring remote from the zome of attachment to the platform, stands proud of the platform. A harness is provided for securing the device to the body of the patient.

Dent in British Pat. No. 1,193,261 discloses a female incontinence device comprising a receptacle consisting of a hollow body portion having a large opening at one end and a tubular opening at the opposite end. The peripheral edge of the large opening is curved to accommodate the user's body said curved periphery having a beading or rim. One end of said large opening is formed so as to extend into the vaginal passage. The appliance is supported in position on the wearer by a harness.

Disabled Living Foundation in British Pat. No. 1,422,638 discloses a female incontinence device provided with a collecting head that in plan tapers from the front end towards the rear end. The head includes a platform surrounding an opening which constitutes the mouth of the urinal and the part of the platform towards the rear boundary of the opening being sloped upwardly and inwardly to provide a hollow arched intralabial extension which locates the head in its correct relationship to the genital anatomy of the user.

Steer in U.K. patent application No. 2,070,936A discloses a female incontinence device including an external resilient pad 18 designed to make sealing engagement with that portion of the user's anatomy that is external to the labia majora and a mount connected to or forming part of the pad. A funnel 12 is carried by the mount pad and dimensioned so that a rim thereof can engage that portion of the user's anatomy which immediately surrounds the meatus of the urethra.

Steer et al. in U.K. patent application No. 2,072,512A disclose a female incontinence device comprising a pad 10 of closed cell polyurethane having a central hole 12 therein. The pad has a funnel like device 26 covering the hole whereby urine can be conducted away.

Sokol in German Offenlegungsschrift No. 1,766,795 discloses a female incontinence device.

MacDougall in European patent application No. 56,318 discloses a female incontinence device intended for long term wear. It includes a tubular sheath 10 integral with a funnel 12 and a urine conducting pipe 14. The sheath is secured to a pad 18 of adhesive material having a central hole leading to the interior of the sheath. The pad is dimensioned so that it can be stuck to the skin of the wearer in the region immediately surrounding the urethral orifice.

In practice, it has proved very difficult to design a female incontinence device with satisfactory leak-proof sealing, especially when the device is being worn by an active person. Another problem encountered but never properly solved is that with some users there may be a sudden rapid flow of urine exiting at considerable pressure. This gives rise to splashing, and the splashed urine may cause soreness and maceration of the skin and also tends to reduce the security of attachment of the device when an adhesive is used. Yet another problem is that many previously suggested devices are undesirably rigid and therefore are both uncomfortable to wear and liable to seal inadequately against the body.

SUMMARY OF THE INVENTION

According to the present invention, there is provided a female incontinence device formed principally of a single piece of flexible material which has a pair of deflectable walls that define a channel or groove at the periphery of the device intended to contact the wearer.

According to the present invention, the device has an overall "waisted" or "8-shaped" configuration as seen in plan to improve comfort in wear.

According to the present invention, a gasket or a liquid repellant non-irritant type of cement or adhesive can be located in the groove defined by the two deflectable walls of the device.

According to the present invention, a female incontinence device is characterized by a body defining a urine-receiving chamber which has peripheral sealing to the user obtained by a groove defined by at least two deflectable walls, and which also has an undercut region located beneath the deflectable walls intended to limit any splashing of discharged urine. The body of the device may define a basin or chamber of downwardly sloping shape so that in use it conducts all discharged urine directly to an outlet pipe.

According to the present invention the deflectable walls of the device as seen in side elevation have sealing edges each of which is constituted by a pair of continuous curves, one on each side of the central longitudinal axis of the device and which extend from a high point at the front of the device to a high point at the rear of the device.

In a preferred embodiment of the invention, the said deflectable walls define a specially shaped saddle configuration designed to contact the wearer between the base of the vagina and the anus and located at the rear zone of the device in order to minimize the possibility of leakage at this area, where the risk of leakage is normally greatest.

BRIEF DESCRIPTION OF THE INVENTION

DETAILED DESCRIPTION OF THE INVENTION

The female incontinence devices illustrated in FIGS. 1-8 are preferably formed, molded or shaped from a single piece of flexible material. Suitable materials include rubber of a Shore hardness of 50°–55°, synthetic rubber substances such as silcone rubber, and flexible synthetic plastics materials.

The devices include a chamber or basin 10 integral with an outlet pipe 12 and a pair of peripheral deflectable walls 14 and 16. They also have a laterally extending flange 18. This flange serves for connection of the device to a suitable woman's garment, for example, a pair of conventional "stretch panties" modified by a cut out in the crotch portion shaped to receive the device. The flange 18 may be stuck or sewn to the panties, to provide a permanent attachment, or it may be attached to suitable panties by press-studs or by strips of material having interengaging hooks, for example the material known by the Trade Name "VELCRO".

Figure 3:
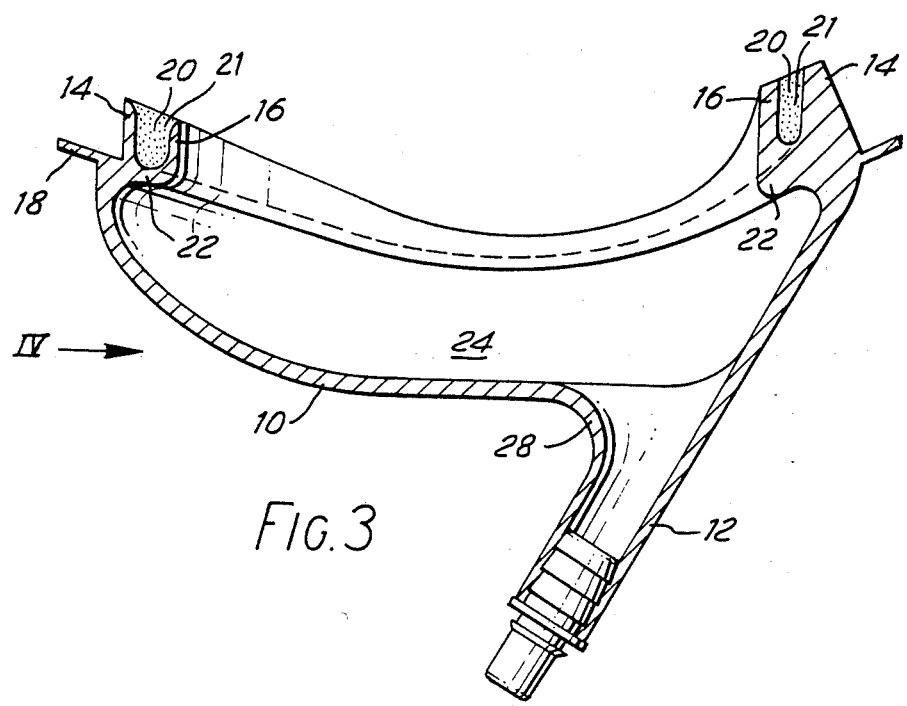
FIG. 3 is a verticle central section taken on the line III of FIG. 2 including a layer of adhesive material.
Figure 7:
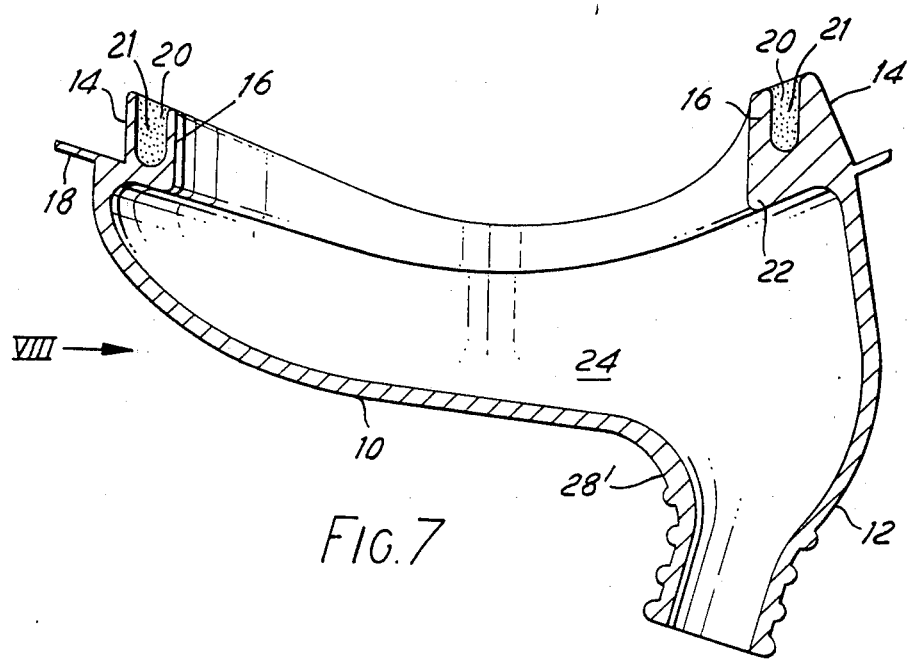
FIG. 7 is a verticle central section taken on the line VI of FIG. 6 including a layer of adhesive material.

According to an advantageous feature of the invention, the periphery of the device intended to contact the skin of the wearer is formed by a pair of deflectable walls 14, 16 defining a groove 20 into which a suitable adhesive material, preferably of a paste nature, may be located. The use of an adhesive material such as an adhesive paste is not essentail although it is preferred. A layer of suitable adhesive material 21 located within groove 20 is shown in FIGS. 3 and 7. The walls 14 and 16 are deflectable and are configured so that they deflect inwardly or outwardly into contact wrth the adjacent surface of the body of the wearer. As a result of this deformation they make surface rather than edge contact with the body and so tend to provide good sealing without undue discomfort.

Alternatively, it is possible to insert a gasket in the form of a soft deformable ring of a thickness chosen so as to fit snuggly within groove 20 between walls 14 and 16. Sealing is then achieved between the upper surface of such a ring, flattened by contact with the body of the wearer, and the confronting skin surface of the wearer. The groove 20 is defined by the walls 14 and 16 and as shown may be deeper and narrower at the rear end of the device (right-hand end of FIGS. 3 and 7) and shallower and wider at the forward end of the device.

According to another particularly advantageous feature of the device, the walls 14 and 16 are supported by a portion of the material 22 which overhangs a urine receiving chamber 24 so defining an undercut region which in use acts to limit splash. In other words, liquid expelled at relatively high pressure runs up the walls of the basin and is turned to move back in a lateral or downward direction. In this way the possibility of any splash reaching the skin of the wearer is greatly reduced.

Figure 4:
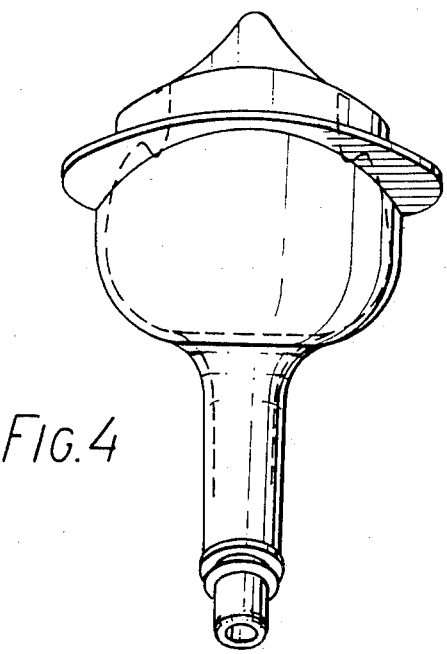
FIG. 4 is an end view of the device looking in the direction of IV in FIG. 3.
Figure 8:
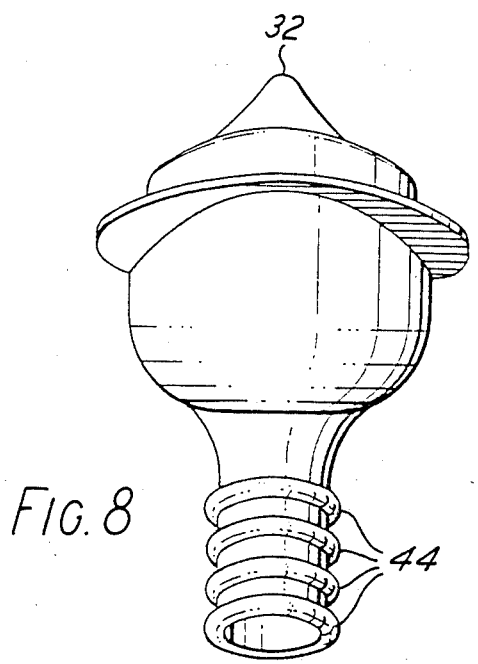
FIG. 8 is an end view of the device looking in the direction of VIII in FIG. 7.

Another advantageous feature of the invention is designed to improve comfort in wear. The illustrated female incontinence devices in accordance with the invention are of "waisted" or "hour glass" shape as seen in plan, as clearly illustrated in FIGS. 2 and 6. The upward facing opening 26 is of like shape, and its boundary is defined by the inner wall 16. As seen in side elevation, the preferred devices have a sealing edge of a specially chosen configuration. Each of the two walls 14, 16 has an upper edge 34, 36 which is a complex curve, rising to a high point at the front of the device and another high point at the rear of the device, so that the overall configuration is reminiscent of that of a saddle. In particular as seen in FIGS. 4 and 8, the walls rise to a rounded cusp or peak 32 which, when the device is worn, is located between the base of the vagina (rearward side) and the anus. In prior art female incontinence devices, this region has presented problems in obtaining effective and adequate sealing. The "waisted" configuration referred to has the result that the device is relatively comfortable to wear both in a standing position as well as a sitting position. This comfort is enhanced by the choice of a flexible rubber or synthetic rubber-type material for the device.

Figure 1:
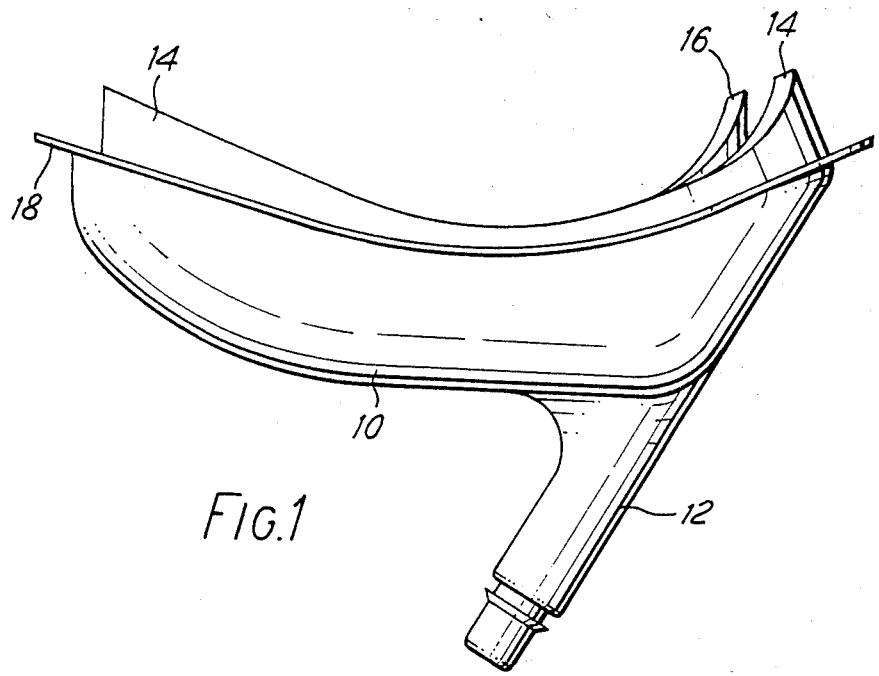
FIG. 1 is a side elevation of one example of a female incontinence device according to the invention.
Figure 2:
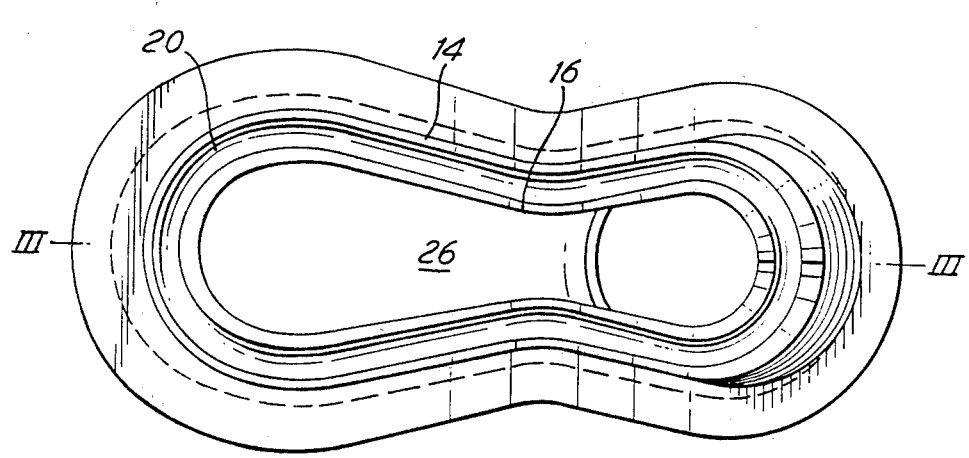
FIG. 2 is a top plan view of the device shown in FIG. 1.

In the embodiment of the device of this invention shown in FIGS. 1 to 4, the basin wall 10, as best seen in FIGS. 1 and 3, defining the lower boundary of the chamber 24 is shaped so as to slope sharply away as seen at 28 in the region of outlet pipe 12. The purpose of this is to facilitate quick and unobstructed flowing away of urine into the outlet pipe 12. As shown in FIGS. 2 and 4, the device may be equipped with a pipe coupling element in accordance with U.K. patent application Ser. No. 2,092,690.

Figure 5:
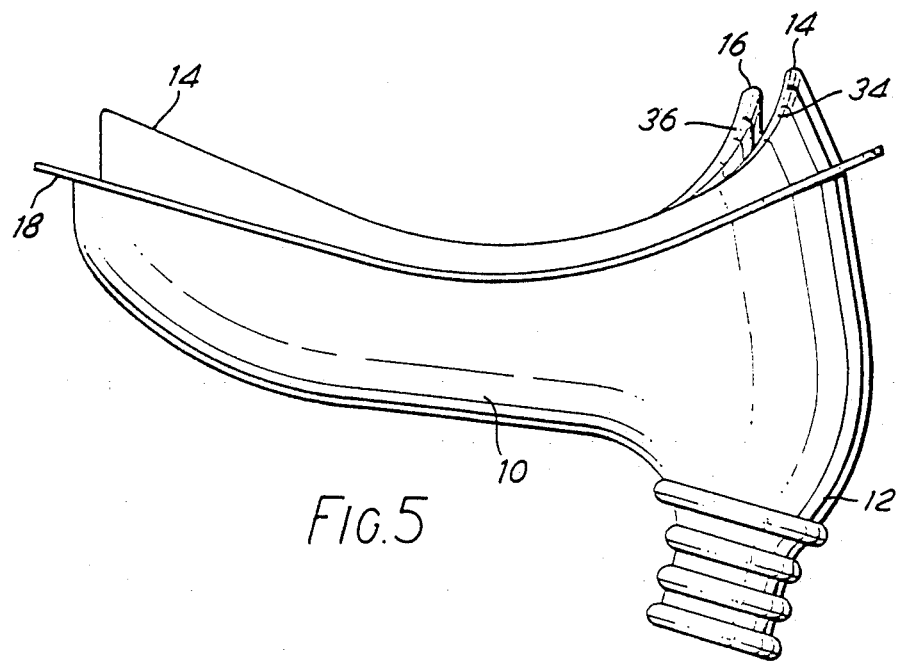
FIG. 5 is a side elevation of another example of a female incontinence device according to the invention.
Figure 6:
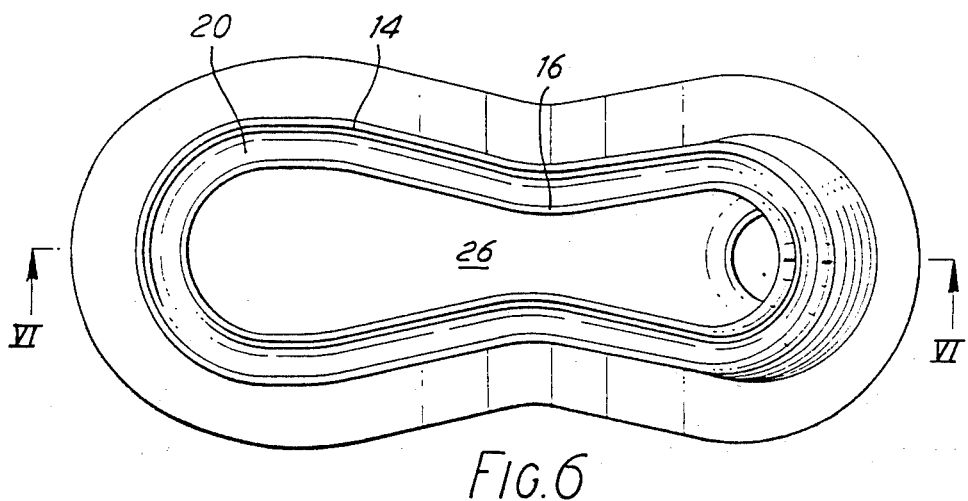
FIG. 6 is a top plan view of the device shown in FIG. 5; p

In the embodiment of the device of this invention shown in FIGS. 5 to 8, the basin wall 10, as best seen in FIGS. 5 and 7, defining the lower boundary of chamber 24 does not slope as sharply as note 28'. Also, outlet pipe 12 shown in this embodiment includes a series of ridges 44 over which a drainage tube can be force fit.

Unlike the prior art female incontinence devices described above, the device of this invention employs the feature of a pair of deflectable walls defining a groove which can receive a sealant. The design of the device of this invention limits splash back and renders the device comfortable to wear. In particular relation to persons liable to discharge urine rapidly at high volume, it is believed that the present incontinence device will prove to be more practical and more satisfactory than prior art designs. In addition, the device can be easily and cheaply manufactured as no assembly is involved. Also, it is relatively simple for a user to apply it to herself, particularly when the device is attached to conventional stretch panties. It is also easy to fill the groove 20 with adhesive paste or with a gasket as described and push the incontinence device into position.

The non-irritant cement or adhesive material referred to above is to be understood as a material which can be squeezed from a tube or molded by hand from a block and which when applied to moist body skin surfaces, is capable of adhesively adhering thereto for a prolonged period of time, for example, well over 12 hours, and which, when so used, does not generate any allergic reaction or irritation in the majority of human being when so adhered. Examples of such materials are disclosed by Chen in U.S. Pat. No. 3,339,546, by Cilento et al. in U.S. Pat. No. 4,166,051 and the paste-like substances disclosed by Chen et al. in European patent application No. 48,556.

What is claimed is:

1. A female incontinence device having a front and rear and a central longitudinal axis therebetween formed principally of a single unitary piece of flexible body compatible material which has a pair of parallel longitudinally upwardly extending deflectable walls which define a groove means for retaining a body adhesive material at the periphery of said device to contact the wearer in the perineal area, a laterally extending flange means for connection of the device to a user's undergarment, said device as seen in plan having a waisted configuration and said deflectable walls as seen in side elevation having sealing top and side edges, each edge of which is constituted by a pair of continuous curves on each side of said axis such that, on each side of the central longitudinal axis of said device, the curves extend from a high point at the front of said device through a low point to a high point at the rear of said device.

2. A device according to claim 1 in which said deflectable walls define a saddle configuration located at the rear zone of said device designed to contact the wearer between the vaginal and anal openings in order to minimize leakage at this area.

3. A device according to claim 2 including an undercut region located beneath said deflectable walls intended to limit splash back.

4. A device according to claim 3 which includes a basin or chamber shaped to conduct urine directly to an outlet pipe.

5. A device according to claim 1 including a layer of adhesive material in said channel or groove to enhance the peripheral sealing.

6. A female incontinence device according to claim 1 characterized by said device also having an undercut region located beneath said deflectable walls intended to limit any splashing of discharged urine.

7. A device according to claim 6 in which said deflectable walls define a saddle configuration located at the rear zone of said device designed to contact the wearer between the vaginal and anal openings in order to minimize leakage at this area.

8. A device according to claim 1 which includes a basin or chamber shaped to conduct urine directly to an outlet pipe.

9. A device according to claim 6 including a layer of adhesive material in said groove to enhance the peripheral sealing.

10. A female incontinence device having a front and rear and a central longitudinal axis therebetween formed principally of a single unitary piece of flexible body compatible material having a pair of parallel longitudinally upwardly extending deflectable walls which define a groove at the periphery of said device to contact the wearer in the perineal area, a laterally extending flange means for connection of the device to a user's undergarment, a layer of adhesive material within said groove to enhance peripheral sealing, said device as seen in plan having a waisted configuration and said deflectable sealing walls as seen in side elevation having sealing top and side edges, each edge of which is constituted by a pair of continuous curves on each side of said axis such that, on each side of the central longitudinal axis of said device, the curves extend from a high point at the front of said device through a low point to a high point at the rear of said device.

11. A device according to claim 10 in which said deflectable walls define a saddle configuration located at the rear zone of said device designed to contact the wearer between the vaginal and anal openings in order to minimize leakage at this area.

12. A device according to claim 11 including an undercut region located beneath said deflectable walls intended to limit splash back.

13. A device according to claim 12 which includes a basin or chamber shaped to conduct urine directly to an outlet pipe.

* * * * *